United States Patent
Garvey et al.

(10) Patent No.: US 9,532,844 B2
(45) Date of Patent: Jan. 3, 2017

(54) CLEANING DEVICE FOR MEDICAL INSTRUMENT AND METHOD OF USE

(71) Applicant: Covidien LP, Mansfield, MA (US)

(72) Inventors: Zachary Thomas Garvey, Stillwater, MN (US); John Robert Moberg, Elk River, MN (US); Lance Nevala, Minneapolis, MN (US); Lucas Schneider, Champlin, MN (US)

(73) Assignee: Covidien LP, Mansfield, MA (US)

( * ) Notice: Subject to any disclaimer, the term of this patent is extended or adjusted under 35 U.S.C. 154(b) by 356 days.

(21) Appl. No.: 14/026,001

(22) Filed: Sep. 13, 2013

(65) Prior Publication Data
US 2014/0190523 A1 Jul. 10, 2014

Related U.S. Application Data

(60) Provisional application No. 61/700,636, filed on Sep. 13, 2012.

(51) Int. Cl.
*A61B 19/00* (2006.01)
*A61M 25/00* (2006.01)
*A61B 17/3207* (2006.01)

(52) U.S. Cl.
CPC .............. *A61B 19/34* (2013.01); *A61B 90/70* (2016.02); *A61B 17/320783* (2013.01); *A61B 2090/701* (2016.02); *A61M 2025/0019* (2013.01)

(58) Field of Classification Search
CPC .............. A61B 19/34; A61B 2019/343; A61B 1/00142; A61B 1/121; A61B 1/125; A61B 1/126; A61L 2/18; A61M 2025/0019; B08B 3/04; B08B 9/02; B08B 1/00
See application file for complete search history.

(56) References Cited

U.S. PATENT DOCUMENTS

| | | |
|---|---|---|
| 1,481,078 A | 1/1924 | Albertson |
| 2,178,790 A | 11/1939 | Henry |
| 2,701,559 A | 2/1955 | Cooper |
| 2,850,007 A | 9/1958 | Lingley |

(Continued)

FOREIGN PATENT DOCUMENTS

| | | |
|---|---|---|
| CA | 2000621 | 4/1990 |
| DE | 3732236 C1 | 12/1988 |

(Continued)

OTHER PUBLICATIONS

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).

(Continued)

*Primary Examiner* — Michael Barr
*Assistant Examiner* — Irina Graf

(57) ABSTRACT

A cleaning device for a medical instrument including a flushing chamber, the flushing chamber having a lumen sized and configured to accept a distal end portion of the medical instrument during a cleaning process. The flushing chamber has an inlet port and an outlet port. Proximal and distal sealing members of the flushing chamber seal about the medical instrument when the instrument is inserted into the lumen of the flushing chamber.

20 Claims, 16 Drawing Sheets

(56) References Cited

U.S. PATENT DOCUMENTS

| | | |
|---|---|---|
| 3,064,651 A | 11/1960 | Henderson |
| 3,082,805 A | 3/1963 | Royce |
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Wilson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundey et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,889,061 A | 12/1989 | McPherson et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinski et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,093,079 A * | 3/1992 | Bakaitis .......... A61L 2/18 134/150 |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |

(56) References Cited

U.S. PATENT DOCUMENTS

| | | |
|---|---|---|
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson et al. |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,511,568 A * | 4/1996 | Bowman ............... A61B 1/121 134/102.2 |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |

(56) References Cited

U.S. PATENT DOCUMENTS

| | | |
|---|---|---|
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,807,340 A * | 9/1998 | Pokras ............... A61M 5/204 604/183 |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,882,589 A * | 3/1999 | Mariotti ............... B08B 3/102 134/102.2 |
| 5,883,458 A | 3/1999 | Sumita et al. |
| 5,888,201 A | 3/1999 | Stinson et al. |
| 5,895,399 A | 4/1999 | Barbut et al. |
| 5,895,402 A | 4/1999 | Hundertmark et al. |
| 5,902,245 A | 5/1999 | Yock |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,979,951 A | 11/1999 | Shimura |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,016,649 A | 1/2000 | Bock et al. |
| 6,019,778 A | 2/2000 | Wislon et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,039,693 A | 3/2000 | Seward et al. |
| 6,048,349 A | 4/2000 | Winston et al. |
| 6,050,949 A | 4/2000 | White et al. |
| 6,063,093 A | 5/2000 | Winston et al. |
| 6,066,153 A | 5/2000 | Lev |
| 6,068,603 A | 5/2000 | Suzuki |
| 6,068,638 A | 5/2000 | Makower |
| 6,081,738 A | 6/2000 | Hinohara et al. |
| RE36,764 E | 7/2000 | Zacca et al. |
| 6,095,990 A | 8/2000 | Parodi |
| 6,099,542 A | 8/2000 | Cohn et al. |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,159,225 A | 12/2000 | Makower |
| 6,165,127 A | 12/2000 | Crowley |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |

(56) References Cited

U.S. PATENT DOCUMENTS

| | | |
|---|---|---|
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antoniades et al. |
| 6,423,081 B1 | 7/2002 | Lee et al. |
| 6,425,870 B1 | 7/2002 | Flesch |
| 6,428,551 B1 | 8/2002 | Hall et al. |
| 6,428,552 B1 | 8/2002 | Sparks |
| 6,443,966 B1 | 9/2002 | Shiu |
| 6,445,939 B1 | 9/2002 | Swanson et al. |
| 6,447,525 B2 | 9/2002 | Follmer et al. |
| 6,451,036 B1 | 9/2002 | Heitzmann et al. |
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 8,226,674 B2 | 7/2012 | Simpson et al. |
| 2001/0000041 A1 | 3/2001 | Seimon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | Van Tassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0191222 A1* | 9/2005 | Lin .................. A61L 2/14 422/300 |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik et al. |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |

(56) References Cited

U.S. PATENT DOCUMENTS

| | | |
|---|---|---|
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |
| 2012/0330336 A1 | 12/2012 | Simpson et al. |
| 2015/0090620 A1* | 4/2015 | Seitz, III ............ A61M 25/002 206/363 |

FOREIGN PATENT DOCUMENTS

| | | |
|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |
| EP | 1 767 159 A1 | 3/2007 |
| EP | 1 875 871 A2 | 1/2008 |
| GB | 2093353 A | 9/1982 |
| GB | 2 115 829 A | 9/1983 |
| GB | 2210965 A | 6/1989 |
| JP | 2-206452 A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | 9316642 A1 | 9/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | WO 00/30531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |
| WO | 2006058223 A2 | 6/2006 |
| WO | 2006066012 A2 | 6/2006 |

OTHER PUBLICATIONS

Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (3 pages).

Brezinski et al., "Optical Coherence Tomography for Optical Biopsy," Circulation, 93:1206-1213 (1996).

Brezinski et al., "Assessing Atherosclerotic Plaque Morphology: Comparison of Optical Coherence Tomography and High Frequency Intravascular Ultrasound," Heart, 77:397-403 (1997).

Huang et al., "Optical Coherence Tomography," Science, 254:1178-1181 (1991).

Jul. 19, 2011 Communication in European Application No. 04760155.4 (5 pages).

Translation of Aug. 15, 2007 mailed Japanese Patent Office Action, Application No. 1999-139033 (4 pages).

* cited by examiner

CLEANING DEVICE FOR MEDICAL INSTRUMENT AND METHOD OF USE

CROSS-REFERENCE TO RELATED APPLICATION

The present application claims the benefit of U.S. Provisional Application Ser. No. 61/700,636, filed Sep. 13, 2012, the entirety of which is hereby incorporated by reference.

FIELD OF THE INVENTION

The present invention relates to a cleaning device for cleaning a medical instrument. More particularly, this invention relates to a cleaning device capable of cleaning residual matter from a distal end portion of a catheter.

BACKGROUND

Medical instruments, including those used in surgical or intravascular procedures require cleaning to remove matter such as plaque, calcium, blood, tissue, and other luminal debris in an effective, efficient and timely manner. However, some medical devices, including catheters, can be difficult to clean quickly and efficiently because of their size and construction.

SUMMARY OF THE DISCLOSURE

Various embodiments of cleaning devices and their methods of use are disclosed. Distinguishing features that may be included in these cleaning devices and methods are described below. It is intended that the cleaning devices and methods may include one or more of these features individually or in combination and it is not intended that the cleaning devices or the methods of use be limited to the specific embodiments described herein.

In one aspect, a cleaning device for a medical instrument includes a flushing chamber. The flushing chamber has a lumen sized and configured to accept a distal end portion of the medical instrument during a cleaning process. The flushing chamber has an inlet port and an outlet port. Proximal and distal sealing members of the flushing chamber seal about the medical instrument when the instrument is inserted into the lumen of the flushing chamber.

DESCRIPTION OF THE DISCLOSURE

Described herein are embodiments of a device and method for cleaning and flushing residual matter from a medical device including but not limited to an intraluminal surgical device including a catheter. Although the various embodiments of the cleaning device are described herein for use in cleaning catheters having catheter bodies adapted for intraluminal introduction the devices may also be used to clean other intraluminal surgical devices or other medical devices of a general nature. In other words, it is not intended that the use of the embodiments described herein be limited to cleaning intraluminal catheters. The dimensions and other physical characteristics of the cleaning device may vary significantly depending on the size and/or physical characteristics of the catheter, surgical instrument, or other medical device to be cleaned.

Figure 1:
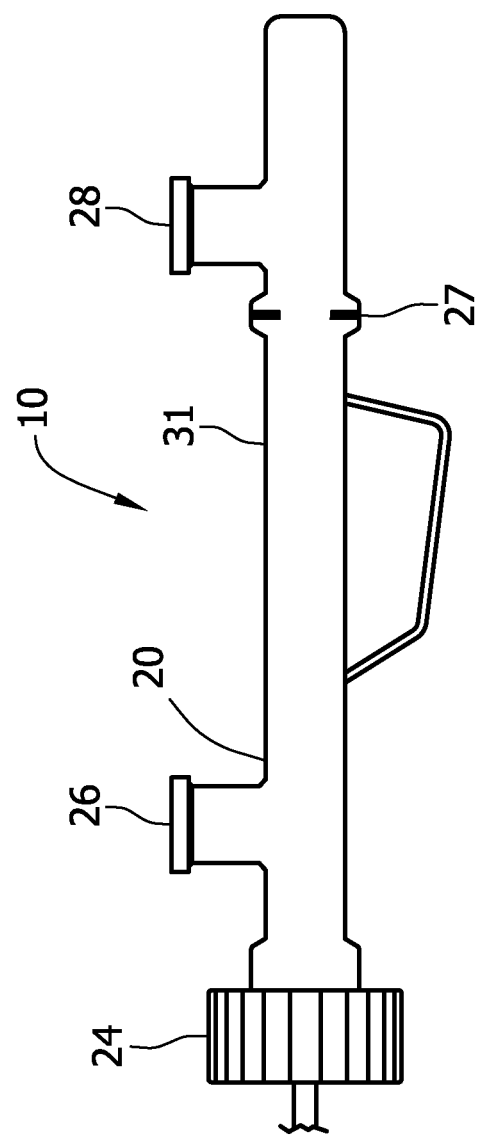
FIG. 1 is a schematic side elevational view of a first embodiment of a cleaning device.
Figure 9:
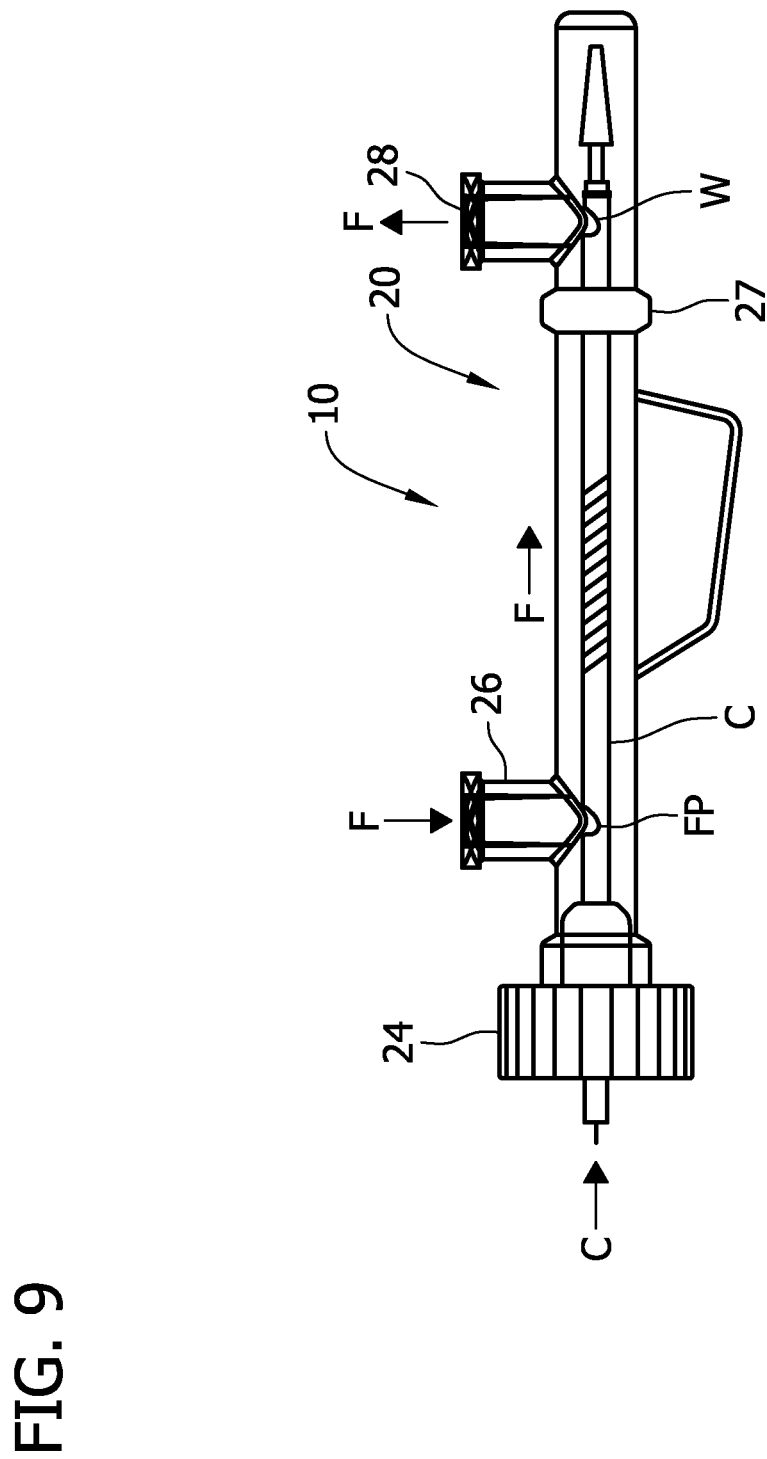
FIG. 9 is a side elevational view of a medical device being cleaned according to a first method of using the first embodiment of the cleaning device.

FIG. 1 depicts a side view of a first embodiment of the cleaning device. A cleaning device 10 is shown and comprises a body that may be elongate in shape and that includes a flushing chamber 20. Flushing chamber 20 may be translucent and may be formed from many well-known plastics. Injection moldings and similar procedures are techniques for manufacturing medical quality tools known in the art. Many materials and manufacturing methods may be utilized to form the body including the flushing chamber. Flushing chamber 20 may be any desired shape or size depending upon the application and may be molded or otherwise constructed in size and shape to house a specific catheter. Flushing chamber 20 contains a distal end 22 and a main lumen 31 that accepts and houses a distal end portion of catheter C. Flushing chamber 20 includes an inlet port 26 and an outlet port 28. For catheters having a side opening such as, for example, a side cutting window W (as shown in FIG. 9), outlet port 28 may be located directly adjacent the cutting window during a cleaning procedure.

Flushing chamber 20 includes a catheter seal or valve 27 positioned between inlet port 26 and outlet port 28. Catheter seal or valve 27 may be any suitable valve or seal, with any desired shape. Catheter seal or valve 27 may further comprise any suitable material and may be, for example silicone. Valves 24 and 27 may be configured to withstand pressures over 100 psi. As will be described in more detail hereafter valve 24 and seal 27 are configured to isolate an inlet opening in the catheter from an outlet opening in the catheter. Valves 24 and 27 prevent fluid flow through the main lumen of the flushing chamber exterior to the body of the catheter being cleaned or flushed. Therefore, any fluid flow through the inlet port 26 and outlet port 28 is directed through an interior lumen or lumens of the catheter.

The dimensions of the flushing chamber 20 may vary in accordance with the size and shape of the catheter to be flushed or cleaned. In particular, the diameter or interior dimension of the main lumen of the flushing chamber should be sized to allow the catheter to be readily inserted and withdrawn without creating an excessively large space to flush. The length of the flushing chamber can be varied to allow the seals of the valve/valves, which are described hereafter, to engage the catheter at appropriate locations. Furthermore, other dimensions of the device may be varied without departing from the scope of the present invention.

Valve 24 is coupled to the proximal end of flushing chamber 20 and when in an open position, accepts a distal end of the catheter to be cleaned. When the catheter has been inserted and is positioned correctly in the flushing chamber, valve 24 is closed and sealably contains the distal end portion of the catheter within the flushing chamber.

Figure 2:
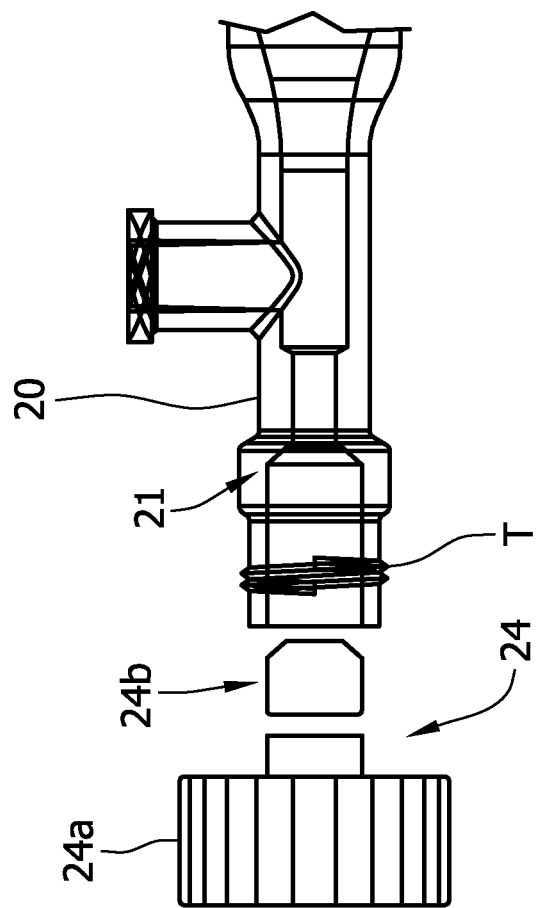
FIG. 2 is an enlarged, fragmentary side elevational view of the cleaning device, showing a valve exploded from a proximal end of a flushing chamber of the cleaning device.
Figure 3:
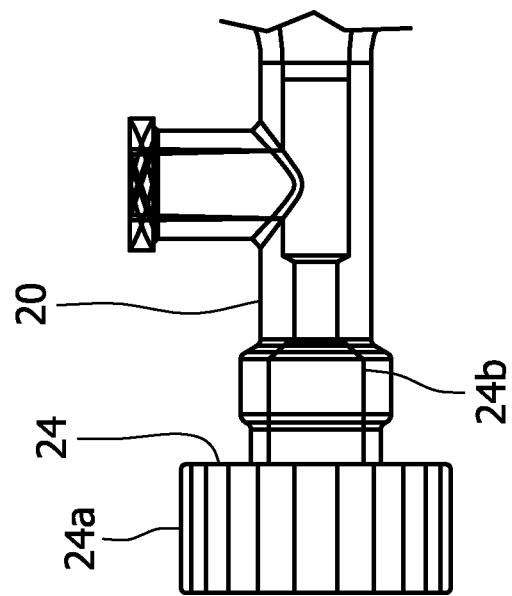
FIG. 3 is an enlarged, fragmentary side elevational view of the cleaning device, showing the valve secured to the proximal end of flushing chamber of the cleaning device.

Valve 24 may have a variety of configurations for sealing the distal end portion of the catheter within the flushing chamber and it should be noted that any suitable valve or seal system/structure may be utilized depending upon the application. FIGS. 2 and 3 depict a side view of the proximal end of flushing chamber 20 coupled to valve or seal 24. Valve or seal 24 may include a threaded cap 24a and a gasket 24b. The proximal end of flushing chamber 20 may be provided with a tapered funnel 21 within the lumen of flushing chamber 20 and threads T on the outer surface of flushing chamber 20 that accept the threads of threaded cap 24a. The distal end of the catheter is inserted into a lumen of threaded cap 24a and then through a lumen gasket 24b.

In use, and as described in more detail with respect to FIG. 9, the distal end of catheter C is inserted and positioned correctly in flushing chamber 20. Threaded cap 24a is then rotated clockwise onto the threads of the proximal end of flushing chamber 20. It should be noted that threaded cap 24a may be rotated counter clockwise depending upon the direction of the threads of threaded cap 24a and the threads on the proximal end of the flushing chamber 20. As threaded cap 24a is rotated, the gasket 24b is axially displaced into the tapered funnel 21 of the flushing chamber 20. The axial displacement causes the inner diameter of gasket 24b to circumferentially compress around the outer diameter of catheter C. The axial displacement of gasket 24b also causes the outer diameter of gasket 24b to circumferentially compress against the inner diameter of tapered funnel 21. The compression of gasket 24b around the outer diameter of catheter C and against the inner diameter of tapered funnel 21 of flushing chamber 20 seals catheter C within the flushing chamber. Gasket 24b in combination with threaded cap 24b, prevent any distal or proximal movement of the distal end of catheter C within the flushing chamber 20.

Figure 4:
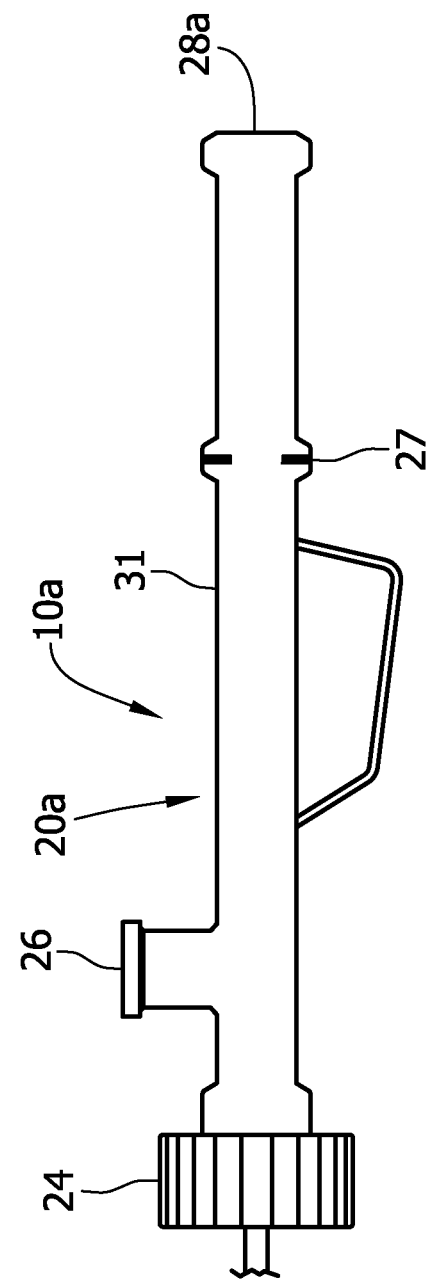
FIG. 4 is a side elevational view of a second embodiment of a cleaning device.

For catheters having one or more distal outlet openings O positioned at or adjacent the distal end of the catheter the outlet port may be located directly adjacent the distal opening/s as in FIG. 4. FIG. 4 shows an alternate embodiment which includes cleaning device 10a with flushing chamber 20a and a method of use thereof. During use catheter C is positioned so that the cutting window, which in this embodiment functions as the inlet port, is between seals 24 and 27 and the opening/s O are distal of seal 27. This ensures that fluid flow into inlet port 26 is directed through an interior lumen or lumens of the catheter and out opening/s O before exiting the cleaning device 10b through outlet port 28a.

Figure 5:
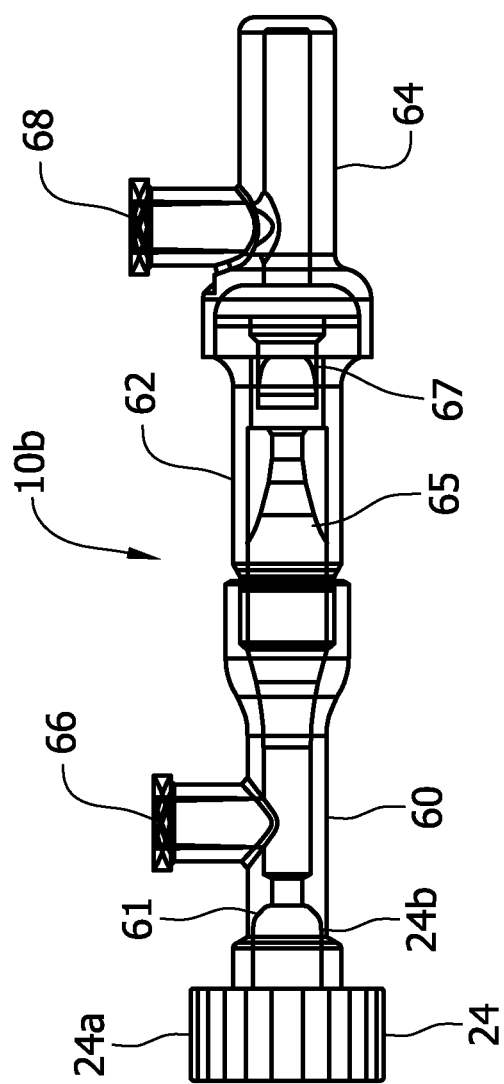
FIG. 5 is a side elevational view of a third embodiment of the cleaning device, the cleaning device having a translucent flushing chamber.
Figure 6:
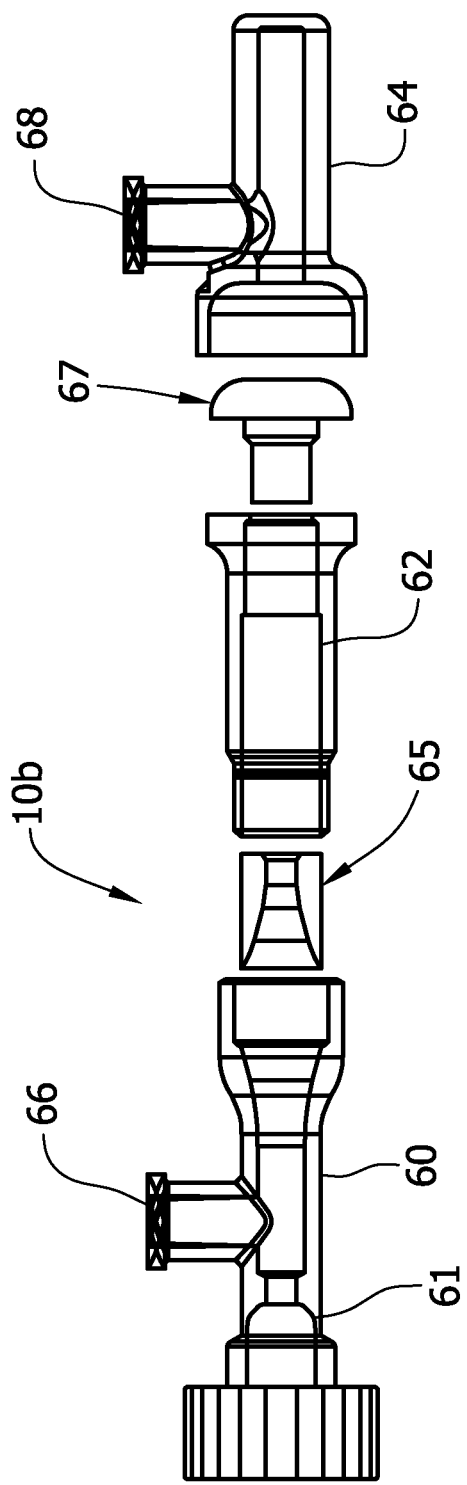
FIG. 6 is an exploded, side elevational view of the third embodiment of the cleaning device.
Figure 8:
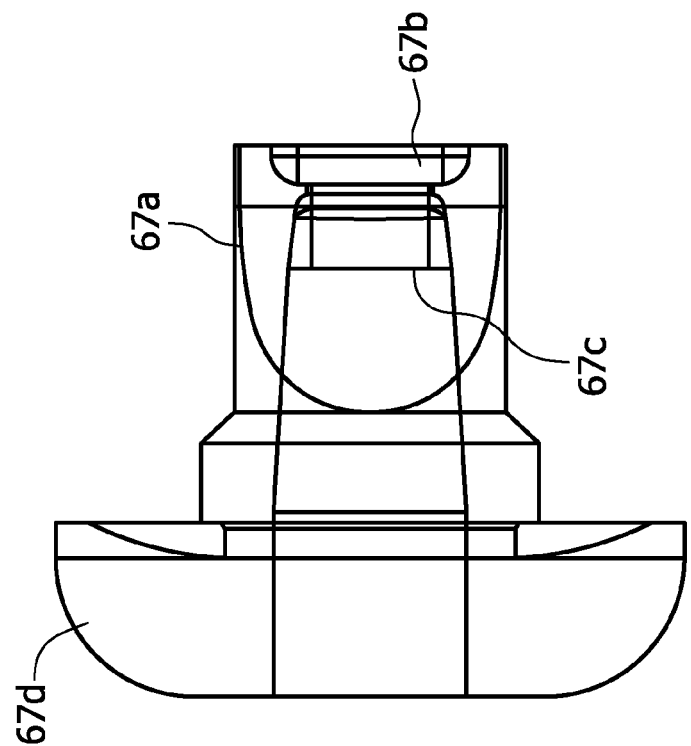
FIG. 8 is an enlarged side elevational view of the valve.
Figure 7:
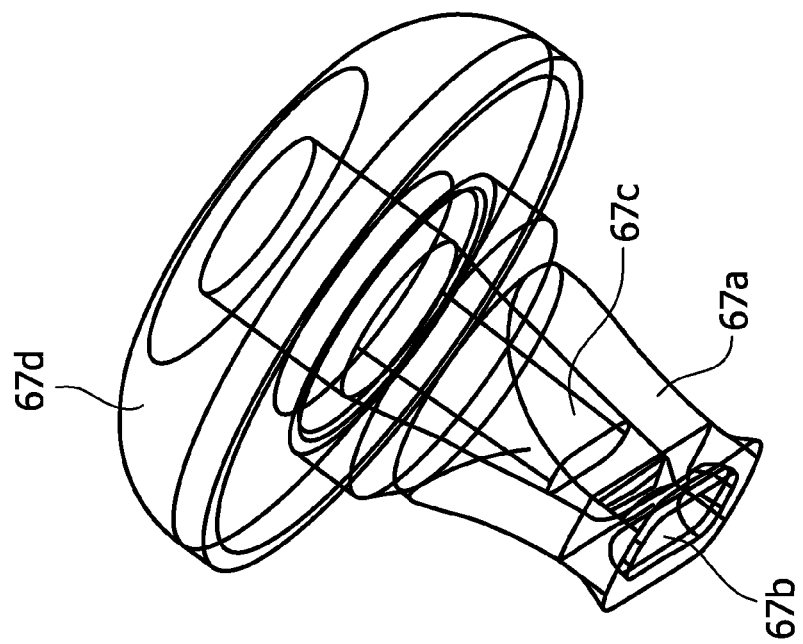
FIG. 7 is an enlarged perspective of a valve of the third embodiment of the cleaning device.

FIGS. 5 and 6 illustrate a substantially similar alternate embodiment of cleaning device 10. Cleaning device 10b has proximal end 60, inlet port 66, outlet port 68, central flush chamber 62, distal chamber 64 and concentricity chamber 65. Proximal end 60 contains tapered funnel 61 that accepts gasket 24b axially displaced by threaded cap 24a. Threaded cap 24a and gasket 24b form valve 24 and prevent proximal and distal translation of catheter C when secured within cleaning device 10b. Concentricity chamber 65 is located within the lumen of central flush chamber 62 and has a tapered lumen that controls the concentricity of catheter C upon insertion into cleaning device 10b. Cleaning device 10b also has duckbill valve 67 which may comprise any suitable material and may be, for example, made from silicone. Duckbill valve 67 may be used in any and all embodiments of the cleaning device described herein and is shown in detail in FIGS. 7 and 8. Duckbill valve 67 has a tapered or 'duckbilled' proximal end 67a and opening 67b located within the lumen of central flush chamber 65. Duckbill valve 67 also has lumen 67c extending from opening 67b to distal end 67d located within a cavity of the proximal end of distal chamber 64. Distal end 67d has a larger diameter than the tapered or duckbilled proximal end 67a. The tapered or duckbilled proximal end 67a conforms around the outer diameter of the catheter C and seals the outer diameter of the catheter C and the inner diameter of central flushing chamber 65 allowing higher fluid pressures during device cleaning and preventing leakage.

FIG. 9 illustrates a method of using cleaning device 10 with a catheter C having a side cutting window W and a flush port FP, located proximal of the cutting window. Such a catheter might have a tissue collection chamber positioned between the cutting window and the flush port. A distal end of catheter C is inserted into the proximal end of flushing chamber 20 and through valve 24 to a position where the cutting window W is distal to seal 27 and the flush port FP is between the seal 27 and the valve 24. Once catheter C has been inserted cutting window W may be aligned adjacently with outlet port 28 (or distal openings O may be aligned adjacently with outlet port 28a as in FIG. 4) and flush port FP may be aligned with inlet port 26, although it should be understood that alignment of the openings and the ports are not required so long as fluid entering through the inlet port is caused to flow into the catheter through the flush port and out of the catheter through the cutting window W, as described below. Valve 24 is closed to form a seal about a proximal portion of the catheter within flushing chamber 20. Seal 27 forms a seal between the outer surface of the catheter and the inner surface of the flushing chamber. Fluid F is then inserted into inlet port 26 and caused to flow from the inlet port into the flush port FP of the catheter, through an interior space in the catheter body and then out of the catheter body through the cutting window W and out of the flushing chamber through outlet port 28. Fluid F may be any suitable liquid and may specifically be water or saline. It should be understood that any suitable gas, such as ambient air, may also be used to flush and/or clean catheter C.

The fluid flow across and through the catheter dislodges and ejects matter such as plaque, calcium, tissue, cellular debris, blood, and other luminal debris from previous catheter use out of the cutting window W of the catheter and through outlet port 28 cleaning catheter C. Fluid F may be caused to flow from the inlet port 26 to the outlet port 27 by introducing the fluid into the inlet port under pressure, by applying a vacuum at the outlet port 28 to create a negative pressure differential between the inlet and outlet ports, or a combination of both. The fluid F flowing through the catheter under pressure and/or suction will remove any unwanted debris or material from the catheter lumen or lumen.

It should also be pointed out that the cleaning device 10 could also be used with a catheter having a flush port FP which is distal to the cutting window W such as in a catheter having a collection chamber distal to the cutting window. In that case the catheter would be inserted such that the flush port FP is positioned distal to seal 27 and cutting window W is between seal 27 and valve 24. The use is the same except that flow through the catheter is into the cutting window and out of the flush port FP.

Figure 10:
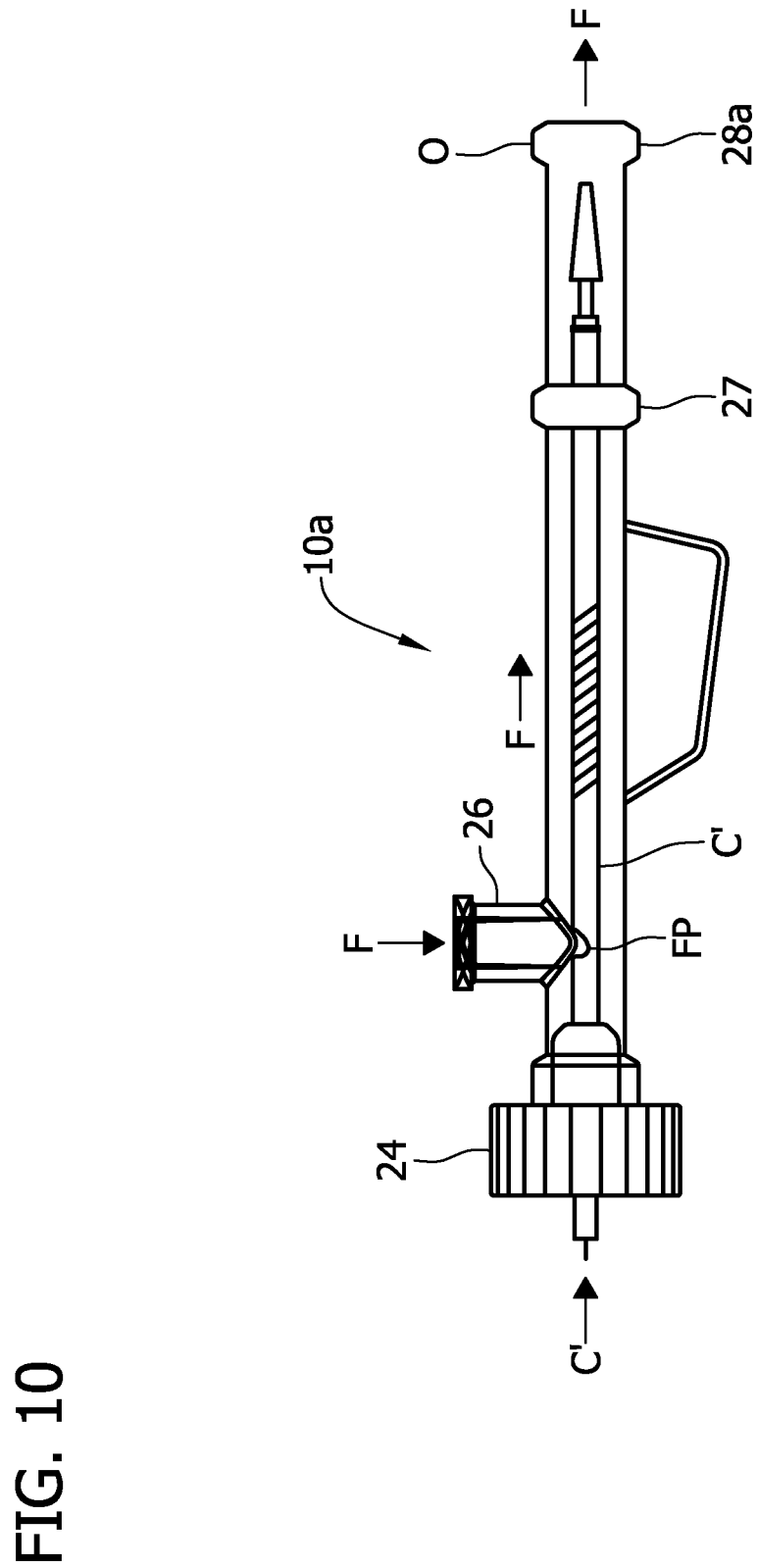
FIG. 10 is a side elevational view of a medical device being cleaned according to a first method of using the second embodiment of the cleaning device.

FIG. 10 illustrates a method of using cleaning device 10*a* with a catheter C' having a distal opening and a flush port proximal of the distal opening. Such a catheter might include catheters having a cutting element which extends through a distal end of the catheter body and a material collection chamber located between the flush port and the distal end of the catheter. A distal end of catheter C' is inserted into the proximal end of flushing chamber 20 and through valve 24 to a position where the opening O is distal to seal 27 and the flush port FP is between the seal 27 and the valve 24. Valve 24 is closed to form a seal about a proximal portion of the catheter within flushing chamber 20*a*. Seal 27 forms a seal between the outer surface of the catheter and the inner surface of the flushing chamber. Fluid F is then inserted into inlet port 26 and caused to flow from the inlet port into the flush port FP of the catheter, through an interior space in the catheter body and then out of the catheter body through the opening O and out of the flushing chamber through outlet port 28*a*.

Figure 11:
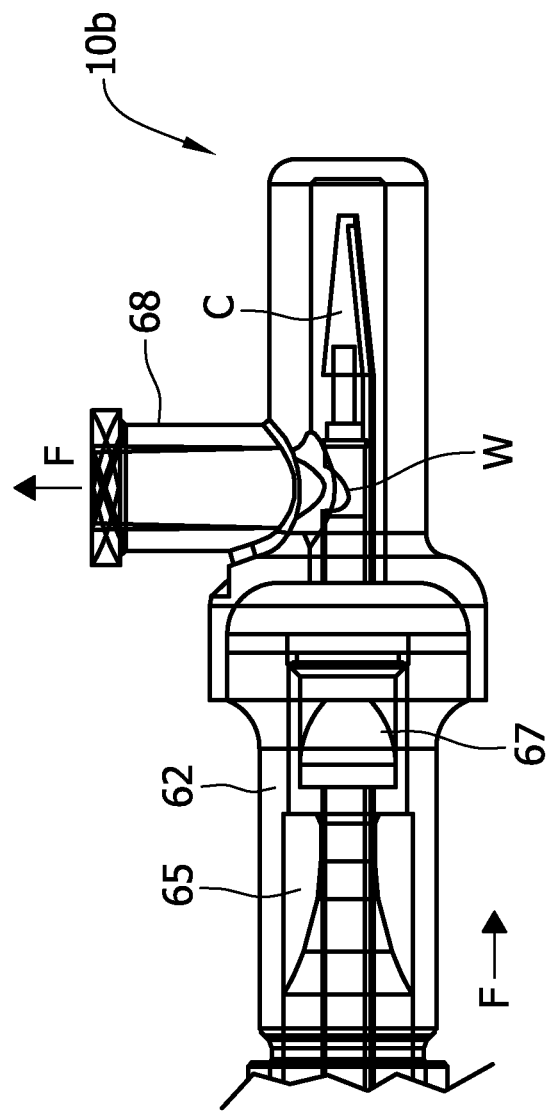
FIG. 11 is an enlarged, fragmentary side elevational view of a medical device being cleaned according to a first method of using the third embodiment of the cleaning device, a flushing chamber being translucent.
Figure 12:
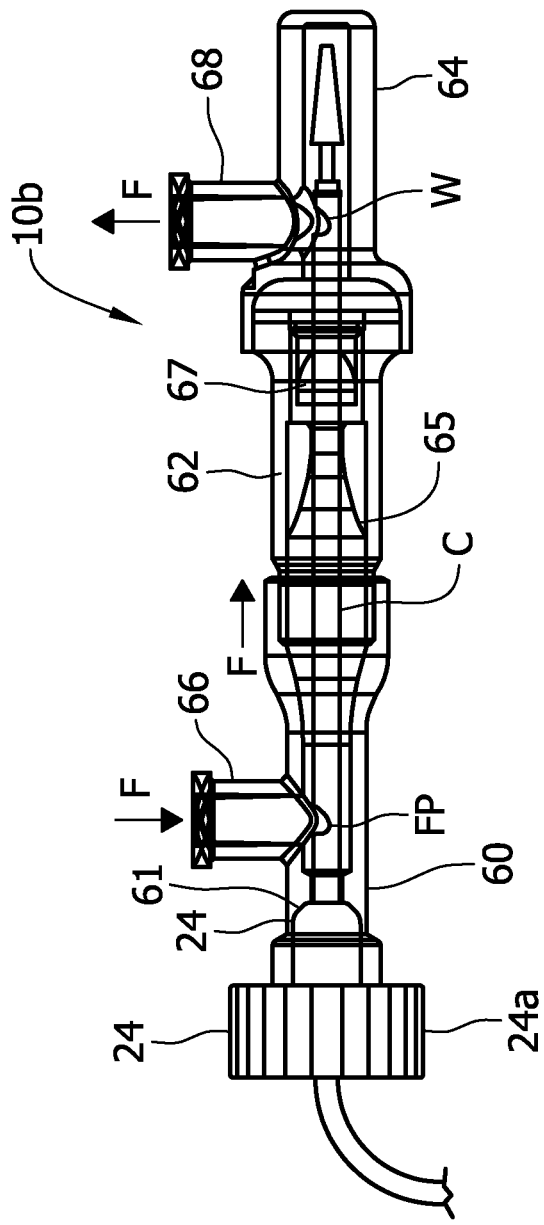
FIG. 12 is a side elevational view of the medical device being cleaned according to the first method of using the third embodiment of the cleaning device, the flushing chamber being translucent.

FIGS. 11 and 12 illustrate a method of using cleaning device 10*b* with a catheter C having a side cutting window W and a flush port FP, located proximal of the cutting window. A distal end of catheter C is inserted through valve 24 which may consist of inserting the distal end of the catheter through a lumen of threaded cap 24*a* and through a lumen of gasket 24*b*. The distal end of catheter C is then inserted into the proximal end 60, through the concentricity chamber 65 of central flush chamber 62 and through duckbill valve 67 into distal chamber 64, positioning the catheter C where the cutting window W is distal to seal 67 and the flush port FP is between the seal 67 and the valve 24.

Once catheter C has been inserted, cutting window W may be aligned adjacently with outlet port 68 and flush port FP may be aligned with inlet port 66, although it should be understood that alignment of the openings and the ports are not required so long as fluid entering through the inlet port is caused to flow into the catheter through the flush port and out of the catheter through the cutting window W, as described below. Valve 24 is closed to form a seal about a proximal portion of the catheter within proximal end 60 of cleaning device 10*c*. The seal may be formed by rotating threaded cap 24*a* clockwise onto threads of proximal end 60. As threaded cap 24*a* is rotated, the gasket is axially displaced into tapered funnel 61 of proximal end 60. The axial displacement causes the inner diameter of gasket 24*b* to circumferentially compress around the outer diameter of catheter C. The axial displacement of gasket 24*b* also causes the outer diameter of gasket 24*b* to circumferentially compress against the inner diameter of tapered funnel 61. The compression of gasket 24*b* around the outer diameter of catheter C and against the tapered funnel 61 seals catheter C within the flushing chamber and gasket 24*b* in combination with threaded cap 24*b* prevent any distal or proximal movement of the distal end of catheter C. Duckbill valve 67 forms a seal between the outer surface of the catheter and the inner surface of central flush chamber 62 and assists in directing fluid flow through the lumen of catheter C.

Fluid F is then inserted into inlet port 66 and caused to flow from the inlet port into the flush port FP of the catheter, through an interior space in the catheter body and then out of the catheter body through the cutting window W and out of the flushing chamber through outlet port 68. The fluid flow across and through the catheter dislodges and ejects matter such as plaque, calcium, tissue, cellular debris, blood, and other luminal debris from previous catheter use out of the cutting window W of the catheter and through outlet port 68 cleaning catheter C. Fluid F may be caused to flow from the inlet port 66 to the outlet port 68 by introducing the fluid into the inlet port under pressure, by applying a vacuum at the outlet port 68 to create a negative pressure differential between the inlet and outlet ports, or a combination of both. The fluid F flowing through the catheter under pressure and/or suction will remove any unwanted debris or material from the catheter lumen or lumen.

It should also be pointed out that the cleaning device 10*b* could also be used with a catheter having a flush port FP which is distal to the cutting window W such as in a catheter having a collection chamber distal to the cutting window. In that case the catheter would be inserted such that the flush port FP is positioned distal to duckbill valve 67 and cutting window W is between duckbill valve 67 and valve 24. The use is the same except that flow through the catheter is into the cutting window and out of the flush port FP.

Figure 13:
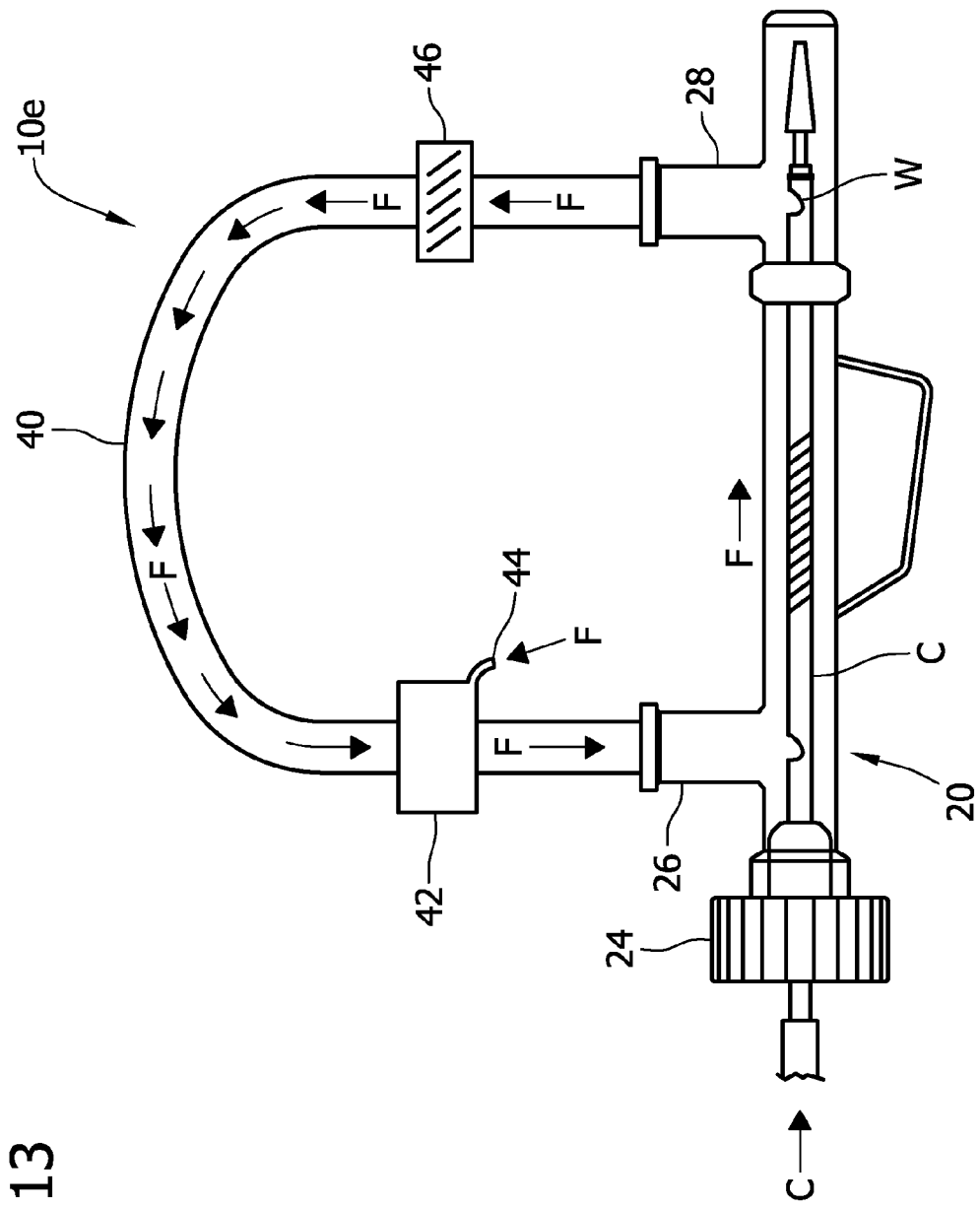
FIG. 13 is a side elevational view of a medical device being cleaned according to a second method of using the first embodiment of the cleaning device.
Figure 14:
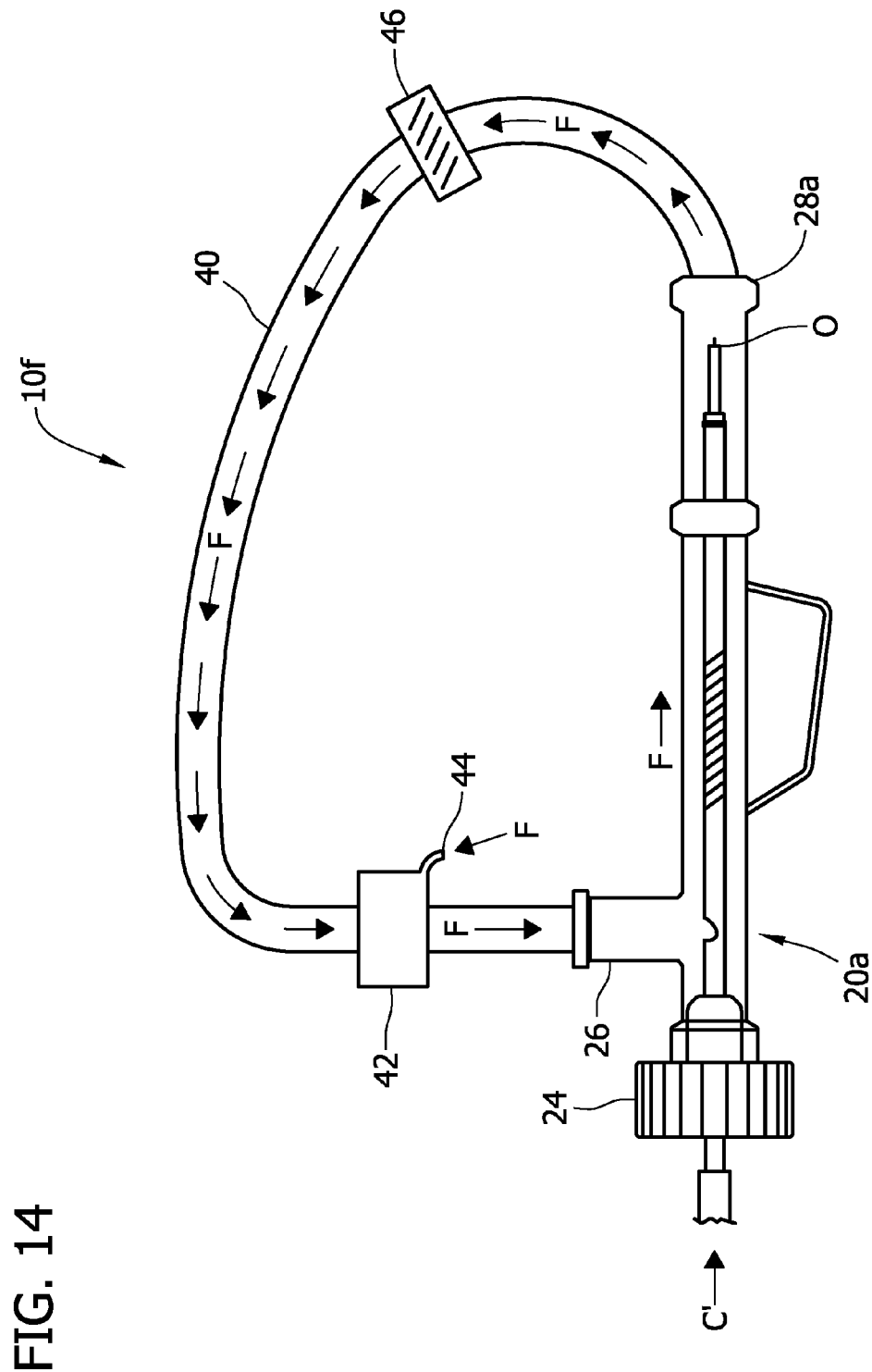
FIG. 14 is a side elevational view of a medical device being cleaned according to a second method of using the second embodiment of the cleaning device.

FIG. 13 depicts a continuous or closed flow cleaning device system that may also be used with the cleaning devices of FIGS. 1, 5, 9, and 12. FIG. 14 depicts a continuous or closed flow cleaning device system that may also be used with the cleaning devices of FIGS. 4, 10 and 20. Each of these embodiments comprise a continuous flow cleaning device and methods of use. Cleaning device 10*e* includes flushing chamber 20 discussed above and is shown in FIG. 13. Cleaning device 10*f* includes flushing chamber 20*a* as discussed above and shown in FIG. 14.

With reference to FIG. 13, cleaning device 10*e* has tube 40 with a first end and a second end. The first end of tube 40 is coupled to inlet port 26 and the second end is coupled to outlet port 28. Pump 42 is coupled to tube 40. Pump 42 may be located adjacent inlet port 40 or other convenient location. Pump 42 may be a peristaltic pump or any other suitable pump as desired and may further be any suitable device for the propulsion of a fluid. Pump 42 may also have a fluid injection port 44 for the injection of fluid into the cleaning device; however it should be noted that the fluid injection port may be located on tube 40 or may be located on flushing chamber 20. Filter 46 is also coupled to tube 40 and may be located adjacent outlet port 28 or other convenient location. Filter 46 may have through holes large enough to allow liquid to travel through easily, but small enough such that bodily tissue material such as plaque, calcium, etc., cannot travel through. Filter 46 prevents the re-circulation of bodily tissue material back into the flush chamber and catheter. In some applications to would be beneficial to the physician or medical practitioner to be able to more easily collect the tissue for evaluation from the cleaning device for evaluation.

With reference to FIG. 14, cleaning device 10f includes flushing chamber 20a discussed above and is shown in FIG. 14. Cleaning device 10f has tube 40 with a first end and a second end. The first end of tube 40 is coupled to inlet port 26 and the second end is coupled to outlet port 28. Pump 42 is coupled to tube 40. Pump 42 may be located adjacent inlet port 40 or other convenient location. A filter, such as filter 46, may be coupled to tube 40 and may be located adjacent outlet port 28a or other convenient location.

The method of using cleaning device 10e includes inserting the distal end of catheter C into the proximal end of the flushing chamber and through valve 24. Once catheter C has been inserted and cutting window W is positioned distal to seal 27, and flush port FP is positioned between valve 24 and seal 27, valve 24 is closed, sealably housing the catheter within flushing chamber. Fluid F is then injected into fluid injection port 44 and pump 42 propels the fluid into inlet port 26 creating a flow of liquid from the inlet port across and through the catheter and towards outlet port 28.

The fluid flow across and through the catheter dislodges and ejects matter from previous catheter use out of the cutting window W of the catheter and through outlet port 28 cleaning the catheter C. The pump propelling the fluid through the inlet port and across and through the catheter may create a type of pneumatic cylinder out of the flushing chamber and creates/increases a negative pressure differential at outlet port 28 that aids in the flushabilty, dislodgement and ejection of residual matter in the catheter between the flush port and the cutting window. Filter 46 catches the matter as it is propelled with the fluid through the outlet port of the flushing chamber and into tube 40 and prevents the matter from being cycled back through the cleaning device and into the catheter. The fluid is propelled through tube 40 and back through inlet port 26 by pump 42.

Cleaning device 10f is used in a similar manner except that catheter C' is inserted with distal opening O located distal of seal 27 and flush port FP located between seal 27 and valve 24. Valve 24 is then closed, sealably housing the catheter within flushing chamber. Fluid F is then injected into fluid injection port 44 and pump 42 propels the fluid into inlet port 26 creating a flow of liquid from the inlet port across and through the catheter and towards outlet port 28a. The fluid flow across and through the catheter dislodges and ejects matter from previous catheter use out of the opening O of the catheter and through outlet port 28a cleaning the catheter C'.

Figure 15:
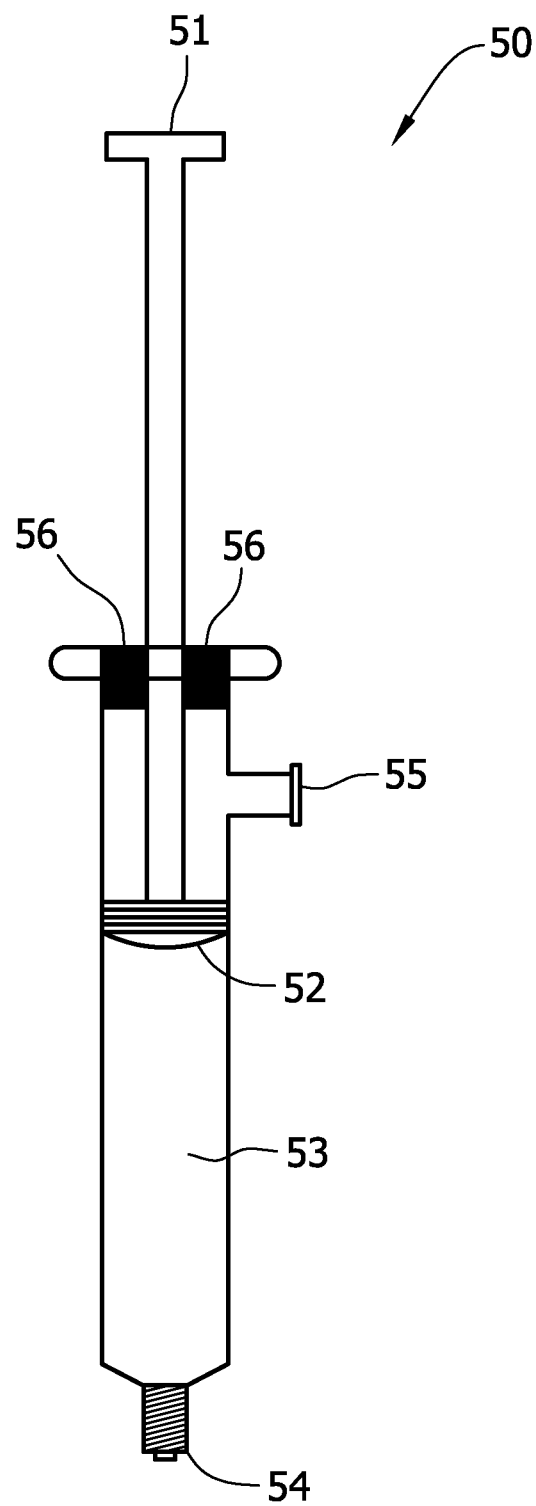
FIG. 15 is a side elevational view of a syringe of an embodiment for use with one or more embodiments of the cleaning device.
Figure 16:
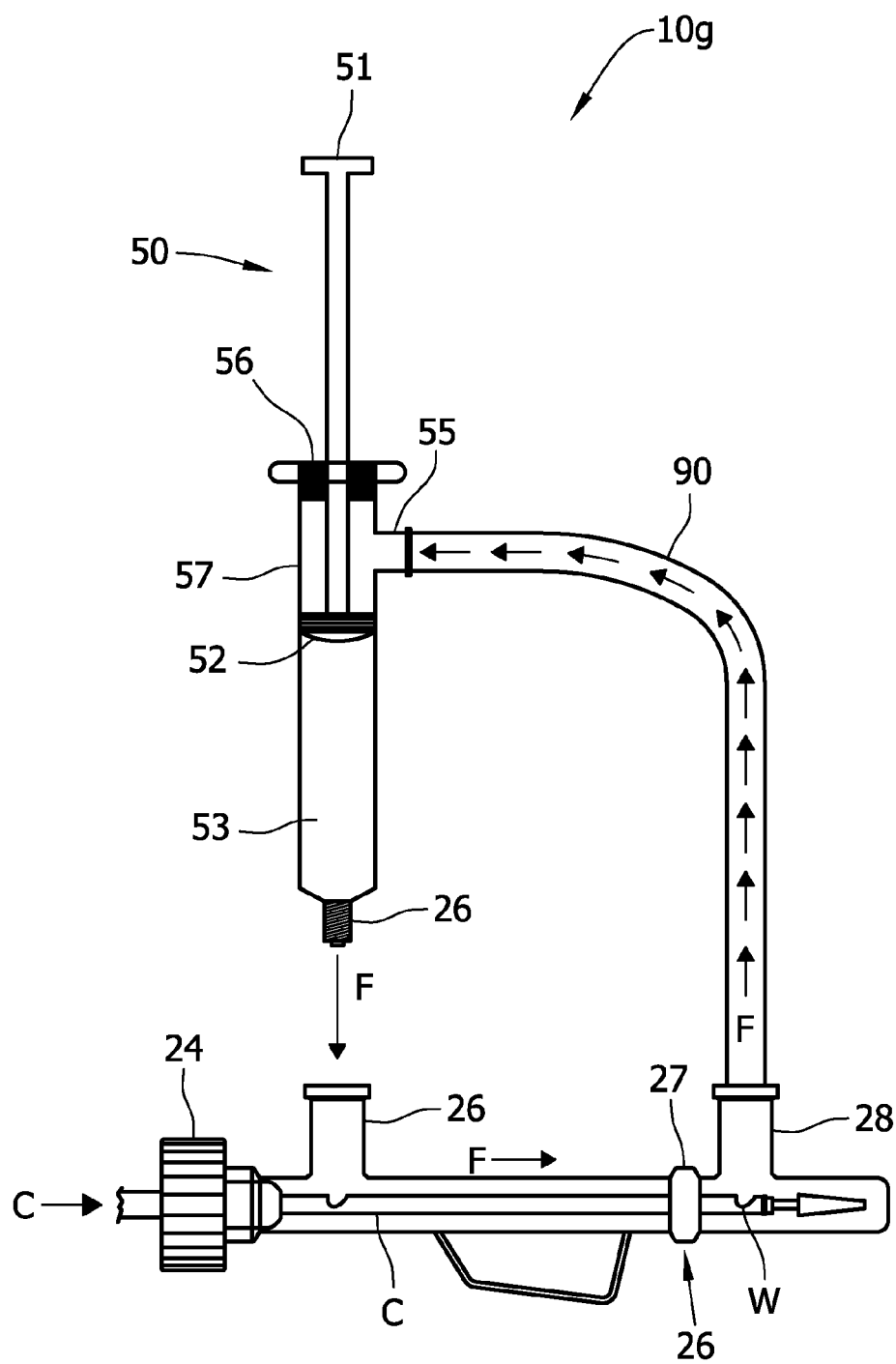
FIG. 16 is a side elevational view of a medical device being cleaned according to a third method of using the first embodiment of the cleaning device.

FIGS. 15 and 16 depict an alternate embodiment of the cleaning device. Cleaning device 10g as shown in FIG. 16, includes flushing chamber 20 (or may also include flushing chamber 20a depending upon the application) discussed above. Cleaning device 10g additionally includes vacuum chamber syringe 50, as shown in FIG. 15, having push rod 51, piston 52 and fluid chamber 53 and fluid outlet 54. Fluid outlet 54 is sized to be received in inlet valve 26 of flushing chamber 20. Syringe 50 also has inlet port 55 and fixed seal 56. Cleaning device 10d has tube 60 with a first end and a second end. The first end of tube 60 is coupled to outlet port 28 and the second end is coupled to inlet port 55 of syringe 50.

The method of using cleaning device log includes inserting the distal end of catheter C into the proximal end of flushing chamber 20 and through valve 24. Once Catheter C has been inserted and cutting window W is properly positioned, valve 24 is closed, sealably housing the catheter within flushing chamber 20. Inlet port 26 of flushing chamber 20 receives fluid outlet 54 of syringe 50. Force is applied to push rod 51 advancing piston 52 into fluid chamber 53 and propelling fluid contained within fluid chamber 53 into inlet port 26 creating a flow of liquid from the inlet port across and through the catheter and towards outlet port 28. As the push rod 51 advances piston 52, a vacuum chamber 57 is created in syringe 51 creating a vacuum and negative pressure differential in tube 90 and outlet port 28 of flushing chamber 20. Thus, in device 10g fluid is input into inlet 24 under pressure and, additionally, a vacuum is applied to outlet port 28 to further enhance fluid flow through the catheter. The fluid flow across and through the catheter dislodges and ejects matter from previous catheter use out of the distal tip of the catheter and through outlet port 28 cleaning the catheter C. The syringe propelling the fluid through the inlet port and across and through the catheter, in addition to the vacuum chamber created by advancing the push rod in the syringe helps create/increase a negative pressure differential at outlet port 28 aiding in the flushabilty, dislodgement and ejection of packing material in the distal tip of the catheter.

Figure 17:
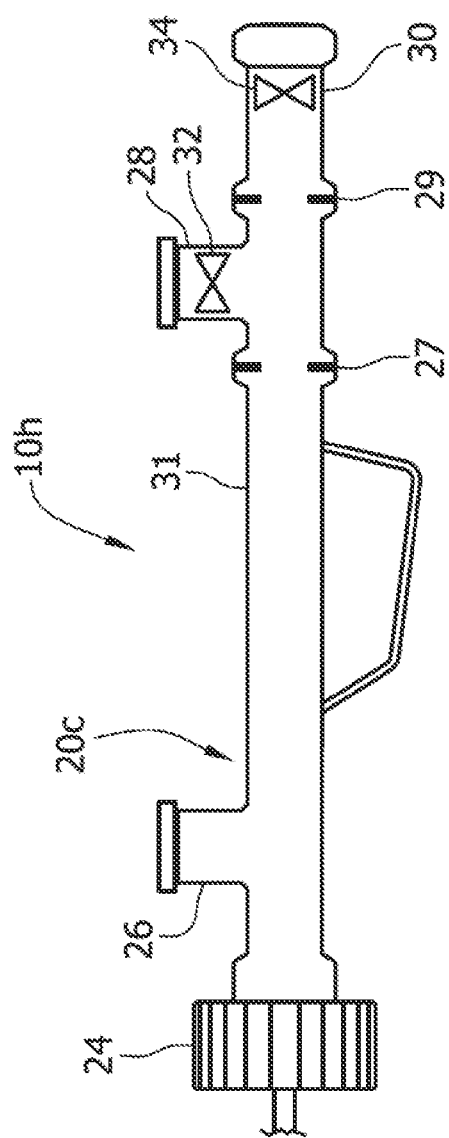
FIG. 17 is a side elevational view of a fourth embodiment of a cleaning device.

FIG. 17 illustrates an alternate embodiment of the cleaning device of the present invention. Cleaning device 10h includes flushing chamber 20c with valve 24 which is located at the proximal end of flushing chamber 20c. When valve 24 is in an open position, a distal end of a catheter may be inserted into the cleaning device 10h. When the catheter has been inserted and is positioned correctly in the flushing chamber, valve 24 is closed and sealably contains the distal end of the catheter within the flushing chamber. Flushing chamber 20c contains a main lumen 31 and also has an inlet port 26, a first outlet port 28 and a second outlet port 30 located at the distal end of the flushing chamber. Flushing chamber 20c may also have a first catheter seal 27 proximal to first outlet port 28 and may also have a second catheter seal 29 proximal of the second outlet port 30 and distal first outlet port 28 that may seal the outer diameter of the catheter and the inner diameter of the flushing chamber. Catheter seals 27 and 29 help to direct the flow of fluid across and through the catheter housed in the flushing chamber and prevent any matter dislodged from the catheter from backing into the flushing chamber proximal the outlet ports, discussed in further detail below. It should be noted that the location, position and number of seals are not limiting and that one catheter seal, additional catheter seals or neither catheter seals may be used. Outlet port 28 and outlet port 30 may have optional stop valves 32 and 34, respectively that may further aid in the direction of fluid flow and may be opened or closed depending on the type of catheter being cleaned, as described in more detail below.

Cleaning device 10h may be used with a catheter having a side opening such as catheter C or a catheter having one or more distal openings, such as catheter C'. A distal end of the catheter is inserted into the proximal end of flushing chamber 20c and through valve 24. Once the catheter has been inserted and the side opening is aligned adjacently with outlet port 28, and the one or more distal openings are aligned with outlet port 30, valve 24 is closed, sealably housing the catheter within flushing chamber 20c. If a catheter such as catheter C is being cleaned valve 32 is opened to create a flow path from the inlet port 26 through the catheter and out the outlet port 28. If a catheter such as catheter C' is being cleaned valve 34 is opened to create a flow path from the inlet port 26 through the catheter and out the outlet port 30. Fluid is then pressurably inserted into inlet port 26 creating a flow of liquid from the inlet port across and through the catheter and towards outlet ports 28 and 30. The fluid flow across and through the catheter dislodges and ejects packing matter form previous catheter use out of the distal tip of the catheter and through outlet ports 28 and 30 cleaning the catheter. Cleaning device 10*h* may be connected for continuous fluid flow similar to devices 10*e* and 10*f* or may be connected for use with syringe 50 as shown in FIG. 16.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents. Further, while choices for materials and configurations may have been described above with respect to certain embodiments, one of ordinary skill in the art will understand that the materials and configurations described are applicable across the embodiments.

The following are non-limiting embodiments, as taught by the above description. One embodiment is a cleaning device comprising a flushing chamber having a proximal end and a distal end, the flushing chamber having a lumen sized and configured to accept and contain a distal end of the medical instrument during a cleaning process; the flushing chamber having an inlet port and an outlet port. A first sealing member is coupled to the flushing chamber, the first sealing member having an open position sized to allow insertion of the medical instrument into the flushing chamber and a closed position in which the first sealing member fluidly seals about an inserted medical instrument. The device further comprises a second sealing member within the flushing chamber between the inlet port and the outlet port, the second sealing member being sized to allow insertion of the medical instrument and being configured to provide a fluid seal between an outer surface of the medical instrument and an inner surface of the flushing chamber during use of the cleaning device.

In another embodiment the cleaning device comprises a flushing chamber having a proximal end and a distal end, the flushing chamber having an interior space sized to house a distal end of a medical instrument during a cleaning procedure; the flushing chamber having an inlet port and an outlet port. A valve is coupled to the proximal end of the flushing chamber, the valve being configured to receive the medical instrument and having a closed position in which the valve fluidly seals about an exterior surface of a medical instrument during a cleaning procedure. A seal is positioned within the interior space of the flushing chamber between the inlet port and the outlet port configured to provide a fluid seal between an outer surface of the medical instrument and an inner surface of the flushing chamber. The embodiment further comprises a tube having a first and second end, the first end coupled to the inlet port of the flushing chamber and the second end coupled to the outlet port of the flushing chamber, the tube and flushing chamber comprising a closed loop fluid circuit. The embodiment also includes a pump in fluid communication with the tube and flushing chamber, a fluid inlet port for injecting a fluid into the fluid circuit, and a filter in fluid communication with the tube and flushing chamber.

In a further embodiment the cleaning device comprises a flushing chamber having a proximal end and a distal end and an interior space configured to receive at least a portion of the medical instrument, the flushing chamber having a fluid inlet port and a fluid outlet port. A first seal is coupled to the flushing chamber and configured to seal about a first portion of the medical instrument and a second seal is coupled to the flushing chamber and configured to seal about a second portion of the medical instrument. A syringe having a fluid chamber containing a fluid and a fluid outlet port is connected to the inlet port of the flushing chamber, the syringe further having a push rod and a piston; and wherein pressure applied to the push rod of the syringe advances the piston in the fluid chamber and injects fluid into the inlet port of the flushing chamber propelling the fluid through the flushing chamber and across and through the distal end of the catheter and wherein residual matter from previous usage of the surgical instrument is dislodged and ejected with the fluid flow out through the outlet port of the flushing chamber.

Another embodiment is a method of cleaning a medical instrument having a lumen with first and second openings comprising:

providing a flushing chamber having a proximal end, a distal end, an inlet port and an outlet port;

providing a proximal seal and a distal seal configured to fluidly seal about first and second portions of the medical instrument, respectively, the proximal seal being proximal of the inlet port of the flushing chamber and the distal seal being positioned between the inlet and outlet ports of the flushing chamber;

inserting the medical instrument into the flushing chamber such that the first opening is between the proximal and distal seals and the second opening is distal of the distal seal, and inserting a fluid into the inlet port of the flushing chamber that creates a pressurized flow of fluid through the inlet port of the flushing chamber, into the first opening in the medical instrument, through the lumen of the medical instrument, out the second opening in the medical instrument and then out through the outlet port of the flushing chamber, wherein residual matter from previous usage of the medical instrument is dislodged and ejected with the fluid flow out through the outlet port of the flushing chamber.

A further embodiment is a method of cleaning an interior portion of a medical instrument comprising:

providing a flushing chamber having a proximal end, a distal end, an inlet port and an outlet port;

providing first and second seals within the flushing chamber, the first seal being configured to seal about a first portion of the medical instrument, the second seal being configured to seal about a second portion of the medical instrument, the first seal being proximal of the inlet port of the flushing chamber and the second seal being positioned between the inlet and outlet ports of the flushing chamber;

providing a tube having a first and second end, a first end coupled to the inlet port of the flushing chamber and a second end coupled to the outlet port of the flushing chamber;

providing a pump in fluid communication with the tube and flushing chamber;

providing a fluid inlet port for injecting a fluid into the cleaning device;

providing a filter in fluid communication with the tube and flushing chamber;

inserting at least a portion of the medical instrument into the flushing chamber;

pumping fluid into the inlet of the flushing chamber, through a first opening in the medical instrument, through the interior portion of the medical instrument, out a second opening in the medical instrument and out of the flushing chamber through the outlet port.

Another embodiment is a method of cleaning a medical instrument comprising:

providing a flushing chamber having a proximal end and a distal end, the flushing chamber being sized to contain at least a distal end of the medical instrument; the flushing chamber having an inlet port and an outlet port;

providing first and second seals within the flushing chamber, the first seal being configured to seal about a first portion of the medical instrument, the second seal being configured to seal about a second portion of the medical instrument, the first seal being proximal of the inlet port of the flushing chamber and the second seal being positioned between the inlet and outlet ports of the flushing chamber;

providing a syringe having a fluid chamber containing a fluid and a fluid outlet port connected to the inlet port of the flushing chamber, the syringe further having a push rod and a piston;

inserting at least a portion of the medical instrument into the flushing chamber so that the distal end of the medical instrument is contained within the flushing chamber;

applying pressure to the push rod of the syringe to advance the piston in the fluid chamber and inject fluid into the inlet port of the flushing chamber, the fluid being propelled through a first opening in the medical instrument positioned between the first and second seals, the fluid being further propelled through an interior portion of the medical instrument and out through a second opening in the medical instrument, the second opening not being positioned between the first and second seals, wherein residual matter within the interior portion of the medical instrument from previous usage is dislodged and ejected with the fluid flow out through the outlet port of the flushing chamber.

What is claimed is:

1. A cleaning device for cleaning a medical instrument, the medical instrument having a distal end portion defining an instrument lumen and proximal and distal openings in fluid communication with the instrument lumen, the cleaning device comprising:

a flushing chamber having opposite proximal and distal ends, a flushing lumen extending between the proximal and distal ends, and distal and proximal ports in fluid communication with the flushing lumen, wherein the flushing lumen is configured to accept the distal end portion of the medical instrument, through the proximal end of the flushing chamber, such that the proximal opening of the medical instrument is generally adjacent the proximal port and the distal opening of the medical instrument is generally adjacent the distal port;

a proximal sealing member coupled to the flushing chamber at a location proximal of the proximal port, the proximal sealing member configured to fluidly seal about the medical instrument when the medical instrument is inserted into the flushing chamber for directing fluid flow between the proximal port and the proximal opening of the medical instrument and inhibiting fluid flow proximal of the proximal sealing member in the flushing lumen; and a distal sealing member coupled to the flushing chamber at a location distal of the proximal port and proximal of the distal port, the distal sealing member configured to fluidly seal about the medical instrument when the medical instrument is inserted into the flushing chamber for directing fluid flow between the distal port and said distal opening of the medical instrument, and inhibiting fluid flow distal of the distal sealing member in the flushing lumen, wherein the distal sealing member comprises a duckbill valve having a tapered proximal end.

2. The cleaning device of claim 1, wherein the flushing chamber is configured such that the proximal opening of the medical instrument is aligned with the proximal port and the distal opening of the medical instrument is aligned with the distal port of the flushing chamber when the medical instrument is inserted into the flushing chamber.

3. The cleaning device of claim 1, further comprising a vacuum source coupled to the distal port of the flushing chamber.

4. The cleaning device of claim 1, wherein the distal port comprises first and second distal ports.

5. The cleaning device of claim 4, wherein the first distal port has a first stop valve having an open position and a closed position and the second distal port has a second stop valve having an open position and a closed position.

6. The cleaning device of claim 1, wherein the proximal sealing member comprises a valve having an open position sized to allow insertion of the medical instrument into the flushing chamber, and a closed position in which the proximal sealing member fluidly seals about the medical instrument when the medical instrument is inserted into the flushing chamber.

7. The cleaning device of claim 1, further comprising:
a tube fluidly connecting the proximal and distal ports of the flushing chamber to at least partially define a closed loop fluid circuit.

8. The cleaning device of claim 7, wherein the tube has first and second ends, the first end coupled to the proximal port of the flushing chamber and the second end coupled to the distal port of the flushing chamber.

9. The cleaning device of claim 8, further comprising:
a pump in fluid communication with the tube and flushing chamber;
a fluid inlet port for injecting fluid into the fluid circuit; and
a filter in fluid communication with the tube and flushing chamber.

10. The cleaning device of claim 9, wherein the pump is coupled to the tube adjacent the proximal port of the flushing chamber.

11. The cleaning device of claim 9, wherein the filter is coupled to the tube adjacent the distal port of the flushing chamber.

12. The cleaning device of claim 1, further comprising:
a syringe having a fluid chamber for fluid and a fluid outlet port fluidly connectable to the proximal port of the flushing chamber, the syringe further having a push rod and a piston, wherein the syringe is configured to inject fluid into the proximal port of the flushing chamber propelling the fluid into the proximal opening of the medical instrument, through the instrument lumen, and out the distal opening of the medical instrument, whereby residual matter from previous usage of the surgical instrument is ejected with the fluid flow out through the distal port of the flushing chamber.

13. The cleaning device of claim 12, wherein the syringe has a syringe inlet port for receiving fluid into the fluid chamber.

14. The cleaning device of claim 13, further comprising a tube fluidly connecting the inlet port of the syringe and the distal port of the flushing chamber.

15. The cleaning device of claim 13, wherein the piston of the syringe divides the fluid chamber into a pressure chamber and a vacuum chamber, the syringe inlet port being in fluid communication with the vacuum chamber.

16. A method of cleaning a medical instrument having a distal end portion defining an instrument lumen, and proximal and distal openings in fluid communication with the instrument lumen, the method comprising:

provproviding a cleaning device including a flushing chamber having opposite proximal and distal ends, a flushing lumen extending between the proximal and distal ends, and distal and proximal ports in fluid communication with the flushing lumen, wherein the flushing lumen is configured to accept the distal end portion of the medical instrument, through the proximal end of the flushing chamber, such that the proximal opening of the medical instrument is generally adjacent the proximal port and the distal opening of the medical instrument is generally adjacent the distal port, a proximal sealing member coupled to the flushing chamber at a location proximal of the proximal port, the proximal sealing member configured to fluidly seal about the medical instrument when the medical instrument is inserted into the flushing chamber for directing fluid flow between the proximal port and the proximal opening of the medical instrument and inhibiting fluid flow proximal of the proximal sealing member in the flushing lumen, and a distal sealing member coupled to the flushing chamber at a location distal of the proximal port and proximal of the distal port, the distal sealing member configured to fluidly seal about the medical instrument when the medical instrument is inserted into the flushing chamber for directing fluid flow between the distal port and said distal opening of the medical instrument, and inhibiting fluid flow distal of the distal sealing member in the flushing lumen, wherein the distal sealing member comprises a duckbill valve having a tapered proximal end;

inserting the medical instrument through the proximal end of the flushing chamber and into the flushing lumen such that the proximal sealing member seals about the medical instrument at a location proximal of the proximal opening of the medical instrument, and the distal sealing member seals about the medical instrument at a location intermediate the proximal and distal sealing members; and introducing fluid into the proximal port of the flushing chamber to create a pressurized flow of fluid through the proximal port of the flushing chamber, into the proximal opening in the medical instrument, through the instrument lumen of the medical instrument, out the distal opening in the medical instrument and then out through the distal port of the flushing chamber, wherein residual matter from previous usage of the medical instrument is ejected with the fluid flow out through the distal port of the flushing chamber.

17. The method of claim 16, further comprising recirculating the fluid flow ejected from the distal port into the proximal port of the flushing chamber.

18. The method of claim 17, further comprising filtering the fluid flow ejected from the distal port to filter out residual matter from the fluid flow before the fluid flow is re-introduced into the proximal port of the flushing chamber.

19. The method of claim 16, further comprising applying a vacuum to direct the fluid flow ejected from the distal port into a chamber.

20. The method of claim 16, wherein said introducing fluid into the proximal port of the flushing chamber comprises connecting an outlet of a syringe to the proximal port and applying pressure to a push rod of the syringe to advance a piston in the fluid chamber of the syringe and inject fluid into the proximal port of the flushing chamber, the method further comprising applying a vacuum within the fluid chamber of the syringe to direct the fluid flow ejected from the distal port into the fluid chamber simultaneously with said applying pressure to a push rod of the syringe.

* * * * *